(12) United States Patent
Brenner et al.

(10) Patent No.: US 7,846,086 B2
(45) Date of Patent: Dec. 7, 2010

(54) DEVICE HOLDING APPARATUS

(75) Inventors: Roland Brenner, Wallhausen (DE); Joachim Steffen, Westhausen (DE); Ottmar Rothaupt, Aalen (DE)

(73) Assignee: Carlzeiss AG (DE)

( * ) Notice: Subject to any disclaimer, the term of this patent is extended or adjusted under 35 U.S.C. 154(b) by 522 days.

(21) Appl. No.: 11/037,797

(22) Filed: Jan. 18, 2005

(65) Prior Publication Data

US 2005/0161176 A1 Jul. 28, 2005

(30) Foreign Application Priority Data

Jan. 27, 2004 (DE) .................. 10 2004 005 094

(51) Int. Cl.
- *A61B 1/00* (2006.01)
- *A61B 1/04* (2006.01)
- *H02G 15/02* (2006.01)
- *H02G 15/08* (2006.01)

(52) U.S. Cl. ............... 600/102; 600/121; 174/77 R

(58) Field of Classification Search ............ 359/510, 359/511; 206/316.1, 305; 128/849; 600/102, 600/119, 121, 122, 124, 125; 174/77 R
See application file for complete search history.

(56) References Cited

U.S. PATENT DOCUMENTS

| | | | | |
|---|---|---|---|---|
| 2,813,692 A * | 11/1957 | Peterson et al. | ............ | 248/56 |
| 2,846,246 A * | 8/1958 | Peras | ............ | 285/124.3 |
| 4,515,333 A * | 5/1985 | Pugh et al. | ............ | 248/123.11 |
| 4,559,052 A * | 12/1985 | Babson | ............ | 604/403 |
| 4,605,400 A * | 8/1986 | Kurtz et al. | ............ | 604/319 |
| 4,735,610 A * | 4/1988 | Akkas et al. | ............ | 604/119 |
| 5,122,904 A | 6/1992 | Fujiwara et al. | | |
| 5,239,981 A | 8/1993 | Anapliotis | | |
| 5,458,132 A | 10/1995 | Yabe et al. | | |
| 5,540,649 A * | 7/1996 | Bonnell et al. | ............ | 600/114 |
| 5,873,814 A | 2/1999 | Adair | | |
| 5,970,980 A | 10/1999 | Adair | | |
| 6,118,076 A * | 9/2000 | Damm et al. | ............ | 174/77 R |
| 6,129,319 A | 10/2000 | Metelski | | |
| 6,805,453 B2 * | 10/2004 | Spetzler et al. | ............ | 359/510 |
| 6,899,307 B2 * | 5/2005 | Strauss et al. | ............ | 248/280.11 |

OTHER PUBLICATIONS

"Two Technical Notes for Microsurgery" by R.F. Spetzler, BNI Quarterly, vol. 4, No. 2, Spring 1988, pp. 38 and 39.

* cited by examiner

*Primary Examiner*—Linda C Dvorak
*Assistant Examiner*—Alireza Nia
(74) *Attorney, Agent, or Firm*—Gerald E. Hespos; Michael J. Porco

(57) ABSTRACT

A holding apparatus is provided for holding a device to be used under sterile conditions. The apparatus includes a holder unit (1) to which the device (3) is to be fixed. The holder unit (1) has a holder portion for fixing a drape (9) so that a held device (3) and the holder portion are substantially air-tightly enclosed. A cavity (2) in the holder unit (1) has a cavity portion (10) for communicating with an intermediate space between a fixed drape (9) and the device (3). A pumping-out device (15) is in the cavity (2) for pumping air out of the cavity portion and the intermediate space. The cavity portion (10) is sealed in the pumping-out operation to prevent the make-up flow of air out of other regions than the intermediate space between a fixed drape (9) and the device (3) or the holder portion.

13 Claims, 4 Drawing Sheets

DEVICE HOLDING APPARATUS

BACKGROUND OF THE INVENTION

1. Field of the Invention

The present invention relates to a device holding apparatus for holding a device which is to be used under sterile conditions and a device arrangement comprising such a device holding apparatus and a device secured thereto which is to be used under sterile conditions. The device holding apparatus can be in particular in the form of a support stand, a ceiling suspension arrangement or a wall suspension arrangement, and the device can be in particular in the form of a medical device, for example an operating microscope.

2. Description of the Related Art

It is important for example in surgery that devices which are used during an operation are sterile in order to avoid infections at the site of the operation. While for example scalpels, spatulas and the like can be readily sterilised other devices which are used during an operation cannot be sterilised readily or indeed cannot be sterilised at all. Such devices include for example monitors and operating microscopes. In order nonetheless to be able to implement sterile conditions during the operation, devices of that kind are covered by a sterile covering, referred to as a drape. In that respect the drape prevents germs from passing into the region of the operation from the non-sterile device.

For example operating microscopes are provided with a drape prior to use in relation to an operation. In that situation the drape encloses the operating microscope and a part of the support stand to which the operating microscope is fixed. So that the drape does not impair the view and the freedom of movement of the doctor performing the operation and his assistant the air is sucked out of the intermediate space between the drape and the microscope and the portion of the support stand which is surrounded by the drape. In that case the drape bears snugly against the microscope and the portion of the support stand so that it no longer represents an impediment to the doctor and his assistant. An operating microscope provided with such a drape is described for example in EP 1 295 568. So that the opening with which the drape is fitted over the portion of the support stand is sealed off in relation to the penetration of air into the interior of the drape, the opening is generally fitted snugly and closely around the portion of the support stand. It is however also possible to provide between the drape and the portion of the support stand a seal which seals off the drape opening in relation to the penetration of air into the region surrounded by the drape, as described in EP 1 295 568.

The object of the present invention is to provide a device holding apparatus for holding a device to be used under sterile conditions, which is advantageously suitable for use together with a drape.

A further object of the present invention is to provide an advantageous device arrangement comprising a device holding apparatus and a device to be used under sterile conditions.

SUMMARY OF THE INVENTION

A device holding apparatus according to the invention for holding a device to be used under sterile conditions includes a holder unit which for example can be in the form of a support stand, a ceiling holding arrangement or wall holding arrangement or in the form of a part thereof, to which the device, for example an operating microscope, is to be directly or indirectly fixed, and which has a holder portion for fixing a drape in such a way that a held device and the holder portion are substantially air-tightly enclosed. In this respect the term air-tightly is not to be interpreted as meaning that no penetration of air whatsoever into the region between the drape and the device or the holder portion is possible, but only to the effect that a pump with a low pump output can already pump out the air which forms a make-up flow thereinto in such a way that the drape can maintain a condition of bearing snugly against the device and the holder portion, once that condition has been implemented.

In addition the device holding apparatus according to the invention includes a cavity which is present in the holder unit and which has a cavity portion which at least partly extends through the holder portion for fixing the drape and which is in communicating relationship with the intermediate space between a fixed drape on the one hand and the device and the holder portion on the other hand.

In addition the device holding apparatus according to the invention includes a pumping-out device arranged at least partly in the interior of the cavity for pumping the air out of the cavity portion and the intermediate space. In that respect the pumping-out device can be for example a pump, a blower or a suction conduit connected to a remotely arranged pump or a remotely arranged blower. A remotely arranged pump or a remotely arranged blower has the advantage in that case over an arrangement in the cavity that vibration due to the pumping operation is not transmitted to the device or is transmitted thereto only to a slight degree.

In the device holding apparatus the cavity portion which is in communicating relationship with the intermediate space between the drape on the one hand and the device or the holder portion on the other hand is sealed off in the air pumping-out operation to prevent the make-up flow of air from other regions than the intermediate space between a fixed drape and the device or the holder portion. In that respect it is already to be viewed as being sealed off if a pump, with just a low pump output, can pump out the make-up flow of air in such a way that the drape can maintain a condition of bearing snugly and closely against the device and the holder portion. The sealing function does not need to be exerted as long as no air is to be pumped out of the intermediate space between the drape and the device or the holder portion respectively.

The invention permits the advantageous use of a drape in relation to a device holding apparatus which has a cavity. Frequently, device holding apparatuses such as for example microscope stands have cavities for example in the form of cable ducts in which supply lines for the device are laid. Cable ducts of that kind are generally not of an air-tight nature and therefore represent flow passages for a make-up flow of air into the pumped-out intermediate space between the drape and the device and the holder portion. A relatively high pump output is necessary however in order to pump out the relatively high air mass flow which subsequently flows as a make-up flow through the cable duct. The high air mass flow and the high pump output however can give rise to vibration of the device holding apparatus, which is not acceptable in all cases. For example vibration of a support stand to which an operating microscope is fixed for neurosurgery can seriously disturb the work being done by the neurosurgeon. In the case of the device holding apparatus according to the invention however the cavity portion which is within the drape is sealed off to prevent the make-up flow of air so that a lower air mass flow occurs into the intermediate space between the drape and the device or the holder portion and accordingly a lower pump output is required in order to pump out the air which flows subsequently as a make-up flow into the intermediate space between the drape and the device or the holder portion surrounded by the drape.

In particular the cavity portion which is in communicating relationship with the intermediate space between a fixed drape and the device or the holder portion is sealed off in relation to the rest of the cavity. If in that configuration a drape extends as far as the location of the holder, at which the sealed-off cavity portion ends, the cavity portion can be sealed off to prevent the make-up flow of air, by means of a sealing arrangement of a relatively simple configuration. A sealing arrangement of that kind can be arranged for example in the cavity in such a way that it sealingly separates the cavity portion from the rest of the cavity. In the simplest case a seal can be used as the sealing arrangement. However it is also possible for the sealing arrangement used to be in the form of a valve which prevents a make-up flow of air from flowing into the cavity portion. In order to enhance the sealing effect, the sealing arrangement can include two or more seals or two or more valves arranged at a spacing from each other. The combination of valves and seals is also possible.

In a configuration of the device holding apparatus according to the invention the holder unit includes a carrier and a cladding fixed to the carrier. In this configuration the cavity is formed between the carrier and the cladding. In particular the cladding can be fixed releasably to the carrier. Removal of the cladding then facilitates access to the cavity for example in order to maintain the sealing element but also for carrying out other maintenance operations, repair procedures or for removing or adding lines. In this configuration the sealing element can be in particular of a resiliently elastic nature. When the cladding is fitted the edge of the sealing element is then pressed by virtue of the spring force against the inside wall of the cladding and thus provides for a high level of sealing action on the part of the sealing element.

In order in the pumping-out operation to facilitate the flow of air from the intermediate space between the drape on the one hand and the device or the holder portion on the other hand into the cavity portion, the holder portion can have through-flow openings to the cavity portion. As however the cavities are usually not air-tight on their own, such through-flow openings are not absolutely necessary. The openings which are caused by manufacture are generally totally sufficient for pumping out the air in the intermediate space between the drape and the device or the holder portion respectively. The speed at which the air can be pumped away with a corresponding pump output can however be increased by additionally provided through-flow openings.

Frequently, the holder units which are used in a holding apparatus according to the invention have further cavities which are generally air-tight, except in regions in which the holder units are pivotably connected together. In an advantageous development of the device holding apparatus according to the invention therefore it includes at least two pivotably interconnected holder units which are connected together by way of a rotary pivot with a closed ball bearing assembly. The rate at which air flows as a make-up flow through the further cavities in the pumping-out operation can be reduced by means of such ball bearing assemblies. That makes it possible to use a comparatively low-output pumping-out device. In addition, this avoids lubricants from being sucked out of the ball bearing assembly.

In addition, there is provided a device arrangement including a device holding apparatus according to the invention. Besides the device holding apparatus according to the invention the device arrangement according to the invention includes a device to be used under sterile conditions, for example a medical device such as for example an operating microscope which is fixed to the holder unit of the device holding apparatus.

In the device arrangement according to the invention the air can be pumped out of the intermediate space between the drape and the device or the holder portion through the cavity portion without in that case a make-up flow of air flowing in relevant amounts from regions other than the intermediate space, into the cavity portion.

Further features, properties and advantages of the present invention will be apparent from the description hereinafter of an embodiment by way of example with reference to the accompanying drawings in which:

DETAILED DESCRIPTION OF THE PREFERRED EMBODIMENTS

An embodiment by way of example of the device holding apparatus according to the invention is described hereinafter with reference to FIGS. 1 to 4. A microscope support stand for holding an operating microscope serves as the embodiment by way of example.

Figure 1:
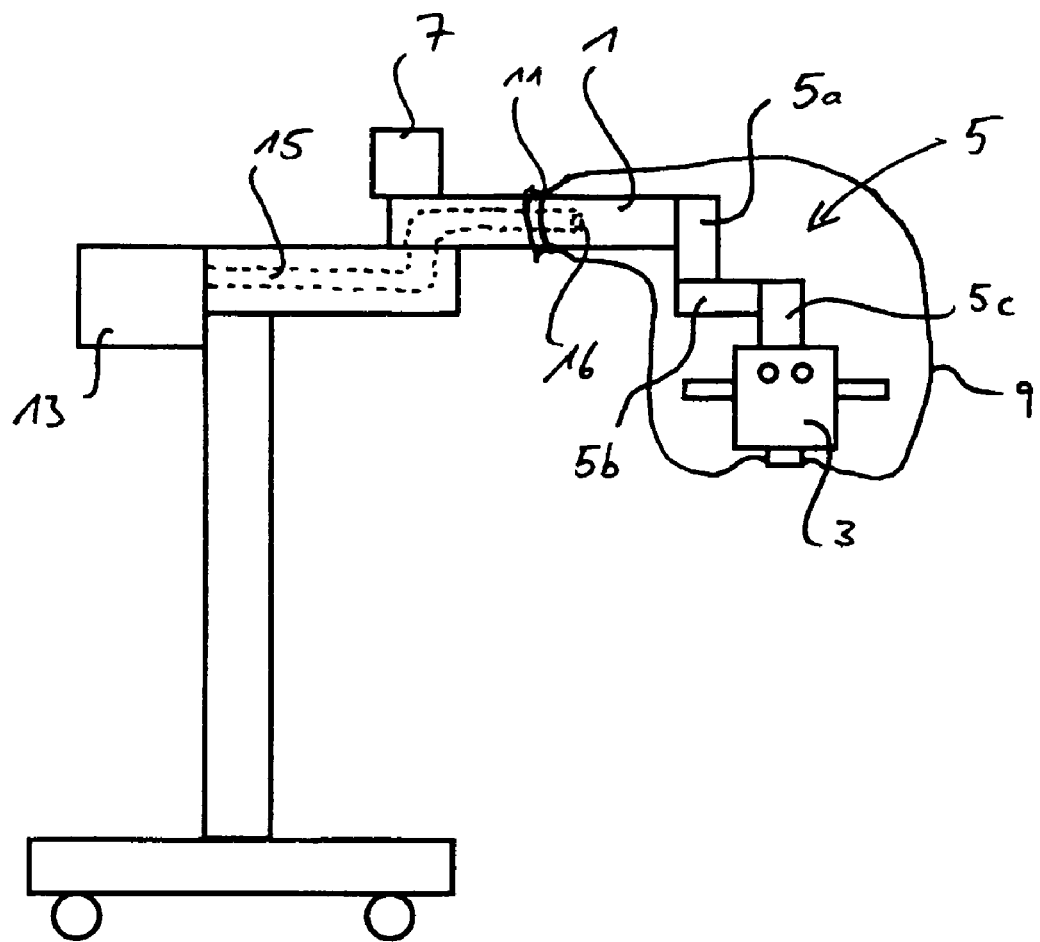
FIG. 1 shows a diagrammatic view of a support stand for an operating microscope as an embodiment by way of example of the device holding apparatus according to the invention.
Figure 2:
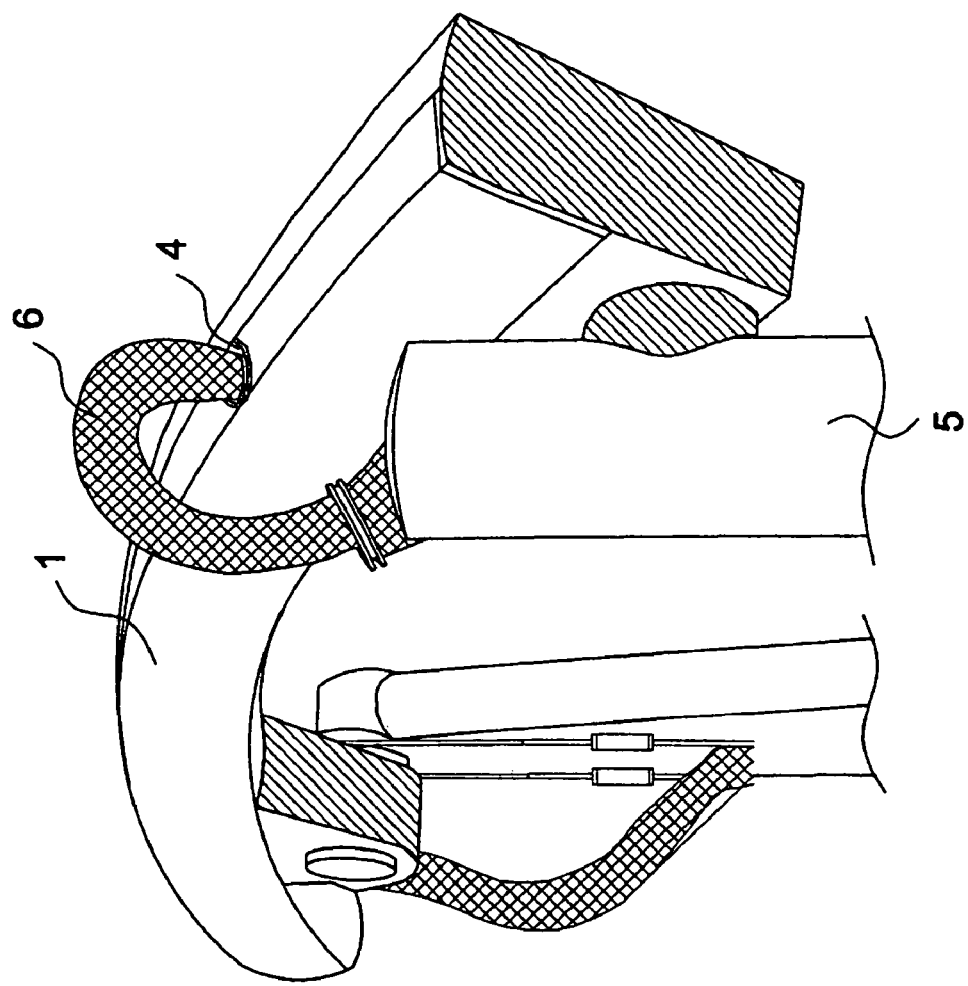
FIG. 2 shows a support stand cantilever arm.

FIG. 1 shows a diagrammatic view of such a support stand. In the illustrated embodiment the support stand as such represents the device holding apparatus. It includes a cantilever arm 1 which serves as a holder unit for an operating microscope 3. The operating microscope 3 is indirectly connected to the arm 1 by way of a microscope suspension means 5 which in the illustrated embodiment includes further holder units 5a-5c. The support stand also includes a supply unit 7 from which cables are passed through the arm 1 to the microscope holder 5. For guiding the cables the arm 1 includes a cable duct 2 which is formed by a cavity extending through the arm 1. From an opening 4 of the cable duct 2 in the arm 1, a cable bundle which is guided in a fabric tube 6 issues from the cable duct 2 and passes into the microscope holder 5. The arm 1 and the microscope holder 5 are shown on an enlarged scale in FIG. 2.

Figure 3:
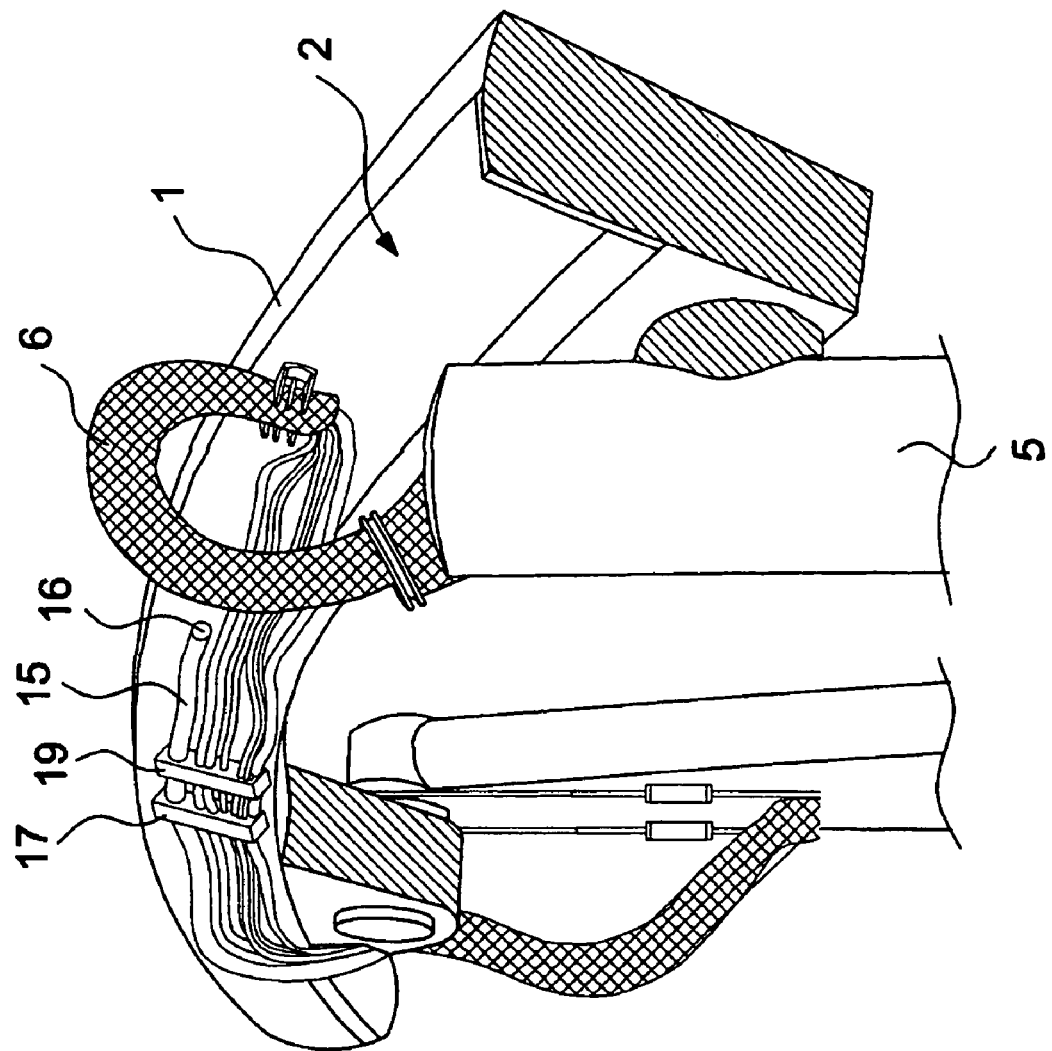
FIG. 3 shows the support stand cantilever arm of FIG. 1 with the cladding removed.

The arm 1 includes a carrier and a cladding which is removably fixed thereto. The cable duct 2 is formed between the carrier and the cladding. FIG. 3 shows the arm 1 with the cladding removed.

If the operating microscope 3 is to be operated under sterile conditions a sterile drape 9 is fitted around the microscope 3, around the microscope holder and around parts of the arm 1 (see FIG. 1). The drape 9 has objective and eyepiece openings so that it does not adversely affect the view on to the site of the operation of the doctor using the operating microscope 3. Those openings are generally of such a nature that they substantially air-tightly seal with the eyepieces or the objective respectively. In addition the drape 9 includes an opening with which it is passed over the arm 1. That opening includes means with which the drape 9 can be substantially air-tightly applied in the region of the opening against the outside surface of the arm 1. Such means can be for example elastic elements. In the illustrated embodiment there is a piece of elastic 11, against the resilient force of which the opening has to be opened when the drape is being fitted over the arm 1. After the drape has been fitted over the arm the piece of elastic 11 then causes the edge of the opening to bear snugly against the arm 1. Instead of a piece of elastic 11 it is also possible to use other means which are suitable for constricting the opening of the drape 9 after it has been fitted over the arm 1 in such a way that in that region the drape bears snugly against the outside surface of the arm 1. For example it is possible to provide cords with which the drape opening can be constricted.

So that the drape 9 does not impede the doctor and his assistant when conducting the operation, after the drape 9 has been fitted the air is pumped out of the intermediate space between the drape on the one hand and the microscope 3, its holder 5 and the arm 1 on the other hand, so that the drape 9 bears snugly against those components and is thus matched to the contours thereof. In that way it is possible to avoid troublesome ridges in the drape. In order to pump the air out of the intermediate space the support stand has a pumping-out device 13, 15 which is at least partially arranged in the interior of the cable duct 2.

In the illustrated embodiment the pumping-out device 13, 15 is in the form of a suction removal device with a ventilating blower 13 arranged at a spacing from the held device and a suction hose 15 connected to the blower 13. The end 16 of the suction hose 15 which is remote from the ventilating blower 13 is disposed in the cable duct 2 of the arm 1. In the present embodiment the whole of the suction hose 15 is passed in the interior of the members of the support stand. It can however also be passed partially outside the members of the support stand as long as its end 16 which is remote from the ventilating blower 13 is disposed in the interior of the cable duct 2. For example the '24VDC-Axial-Lüfter TYP 4414 FM' from Pabst-Motoren GmbH & Co KG, St Georgen, Germany, is suitable as the ventilating blower. The pumping-out device however does not necessarily need to include a ventilating blower. Basically, any system with which a fluid can be pumped can be used in the pumping-out device, for example a combination of a vacuum pump and a suction hose.

Figure 4:
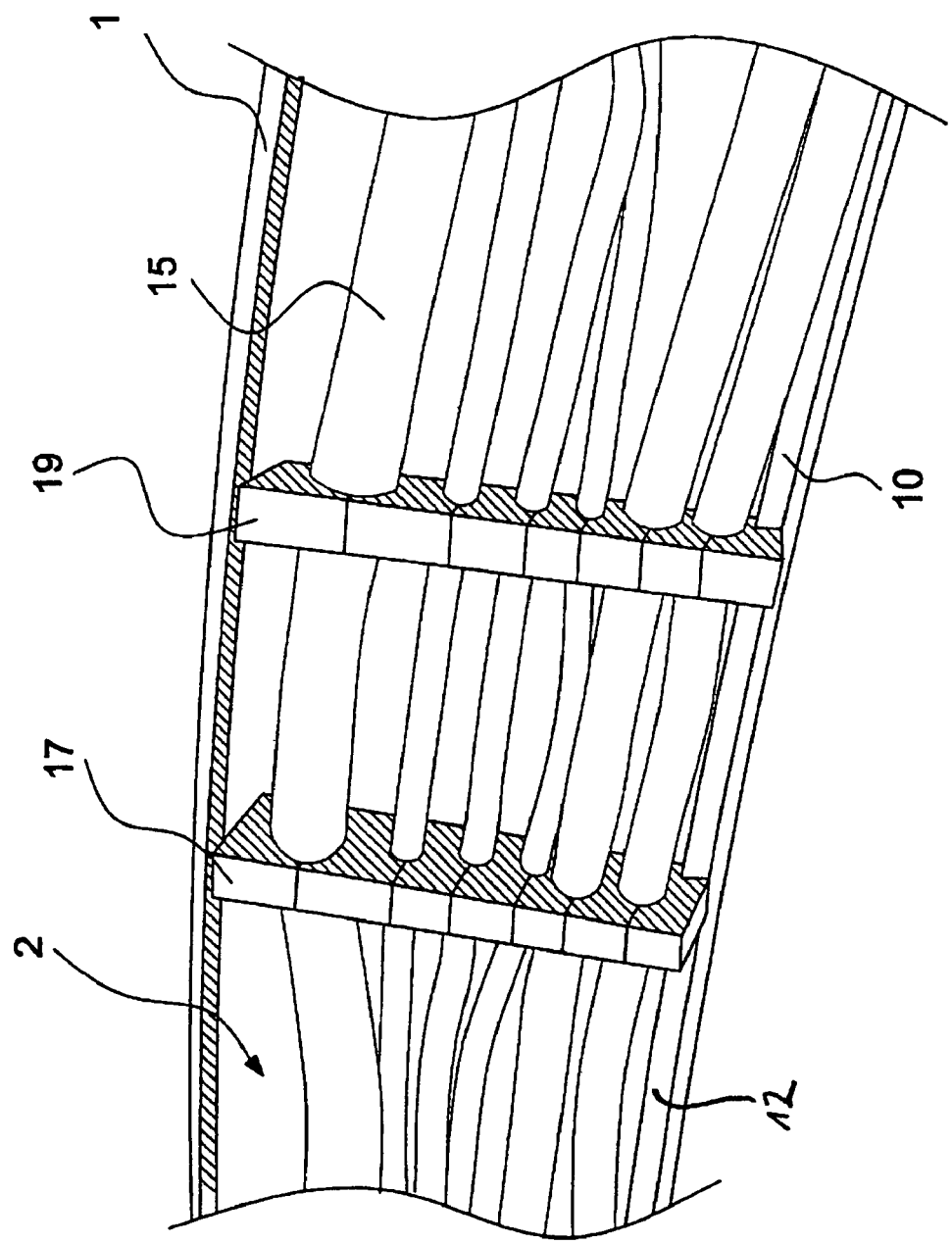
FIG. 4 shows a view on an enlarged scale of a portion from FIG. 3.

Arranged in the cable duct as a sealing arrangement are two foam seals 17, 19 which extend over the entire cross-section of the cable duct 2 and have passage means for the cables and for the suction hose 15 to pass therethrough (see FIGS. 3 and 4). The sealing arrangement subdivides the cable duct 2 into a front portion 10 towards the microscope holder 5 and a rear portion 12 towards the pump 13.

When the cladding is fitted on to the carrier of the arm 1 the elastic foam seals 17, 19 adapt to the internal contour of the cladding so that they bear sealingly against the inside wall of the cladding. The front portion 10 of the cable duct is then sealed off in relation to the rear portion 12 of the cable duct.

For mounting to the device holding apparatus according to the invention the drape 9 is fitted over the microscope 3, the microscope holder 5 and a part of the arm 1 in such a way that the drape 9, as viewed from the microscope holder 5, extends to the seals 17, 19. The piece of elastic 11 provided at the drape opening causes the drape 9 to bear sealingly against the outside surface of the arm 1, in the region of the seals 17, 19.

For pumping the air out of the drape the ventilating blower 13 with a relatively high pump output is set in operation so that the air is quickly sucked out of the front portion 10 of the cable duct 2 by means of the suction hose 15. As the cable duct 2 is not of an air-tight nature, that results in a make-up flow of air subsequently flowing from the intermediate space between the drape 9 and the microscope 3 and its holder 5 or the arm 1 into the front portion 10 of the cable duct 2 and from there into the suction hose 15 until the air has been sucked out of the intermediate space. As soon as that has happened, the pump output can be reduced as it is now only necessary for the air which is a make-up flow through leakage points to be still sucked away. In that situation the foam seals 17, 19 prevent air from subsequently flowing out of the rear portion 12 of the cable duct 2 into the front portion 10 of the cable duct 2.

In order to make it easier to find the foam seals 17, 19 when fixing the drape opening by means of the piece of elastic 11, a marking can be provided on the outside of the arm 1, which marks the position of the foam seals 17, 19.

In the present embodiment the device holding apparatus according to the invention has been discussed and described by reference to a support stand. The device holding apparatus however does not have to be in the form of a support stand. For example it can also be in the form of a ceiling or wall suspension arrangement. It is also not necessary to use two foam seals for sealing off the front portion of the cable duct in relation to the rear portion thereof. It is in principle sufficient to use a single seal as the sealing arrangement.

Instead of one or more seals it is also possible to use one or more valves. If the valves are so designed that they check a flow only in one direction, they are arranged in the cross-section of the cable duct in such a way that they prevent air from flowing into the front portion of the cable duct but permit air to flow out of that portion. Valves which check only in one direction mean that the introduction of air into the intermediate space between the drape and the device or the arm can be facilitated. The introduction of air is desired for example when, after use of the device, the drape is to be removed as quickly as possible as in that way the reduced pressure which has been produced between the drape and the arm or the device can be removed more quickly.

In addition it is possible to use as the pumping-out device, instead of a suction removal device with a ventilating blower arranged remotely from the front portion and a suction hose, a blower which is arranged in the region of the front portion of the cable duct and a gas discharge conduit which leads from that portion and through which the blower blows the air out of the front portion.

In order to facilitate the flow of air from the intermediate space between the drape and the arm or the device fixed to the arm into the front portion of the cable duct, through-flow openings can be provided in the cladding of the arm. As however the cable duct is generally not air-tightly sealed off, the provision of through-flow openings is however not absolutely necessary.

In general the carrier of the arm and the holder units 5a-5c of the microscope holder 5 have further cavities which are substantially air-tight except in the regions in which the carrier and the holder units 5a-5c are pivotably connected together. In order to prevent the subsequent make-up flow of air through the pivot locations, in the embodiment illustrated the rotary pivot between the holder unit 5b and the holder unit 5c has a closed ball bearing assembly. It will be appreciated also that all rotary pivots may have such a ball bearing assembly. For example a groove ball bearing assembly with cover or sealing discs in accordance with DIN 625 can be used as a closed ball bearing assembly in a rotary pivot. Such ball bearing assemblies can be obtained for example from AB SKF, Gothenburg, Sweden or FAG Kugelfischer Georg Schäfer AG, Schweinfurt, Germany.

Instead of the cable duct, it is also possible to use other cavities extending through the arm 1 for pumping the air out of the space enclosed by the drape insofar as those cavities are in communicating relationship with the space enclosed by the drape.

Finally it is also possible for the cable portion or cavity portion which, when a drape is fitted, is disposed outside the space enclosed by the drape, to be air-tight. It is then possible to omit an intermediate space between the two cavity portions or cable duct portions.

What is claimed is:

1. A microscope support stand for holding a microscope to be used under sterile conditions comprising:
    an arm (1) to which the microscope (3) is to be indirectly or directly fixed and which has a holder portion for fixing a drape (9) in such a way that the microscope (3) and the holder portion are substantially air-tightly enclosed,
    a cable duct (2) in the arm (1) and having a front portion (10) forward from the holder portion for fixing the drape (9) and which is in communicating relationship with an intermediate space between the fixed drape (9) and the microscope (3) or the holder portion, the cable duct (2) further having a rear portion (12) rearward of the holder portion,
    a pumping-out device (15) which comprises a suction hose that is arranged at least partly in the interior of the cable duct (2) for pumping air out of the front portion (10) and the intermediate space between the drape (9) and the microscope (3) or the holder portion, and
    front and rear resiliently elastic seals (19, 17) in sealing engagement with inner peripheral surface regions of the cable duct (2) across two axially spaced entire cross sections of the cable duct (2), each of the seals (19, 17) including passages for cables and the suction hose (15) and being arranged in the cable duct (2) between the front portion (10) and the rear portion (12) and at a position substantially aligned with the holder portion of the arm (1) for fixing the drape (9) so that the seals (17, 19) seal the front portion (10) from the rear portion (12) in a pumping-out operation by the pumping-out device (15) to prevent a flow of air from the rear portion (12) into the front portion (10) so that a lower output of the pumping-out device (15) is required to offset a make-up flow of air into the intermediate space.

2. The microscope support stand of claim 1 characterised in that the front portion (10) which is in communicating relationship with the intermediate space between the drape (9) and the microscope (3) or the holder portion includes through-flow openings for air to pass therethrough.

3. The microscope support stand of claim 1 characterised in that the arm includes at least two pivotably interconnected holder units which are connected together by way of a rotary pivot with a closed ball bearing assembly.

4. The microscope support stand of claim 1 characterised in that it is in the form of a floor support stand, a ceiling suspension arrangement or a wall suspension arrangement.

5. An arrangement comprising the microscope support stand of claim 1 and a microscope (3) fixed to the arm (1) and to be used under sterile conditions.

6. The arrangement of claim 2 characterised in that the microscope is an operating microscope.

7. The microscope support stand of claim 1, wherein the arm further includes at least one marking at a location substantially aligned with the seals for identifying a position of the holder portion for fixing the drape (9).

8. A microscope support stand for holding a microscope to be used under sterile conditions comprising:
    an arm (1) to which the microscope (3) is to be indirectly or directly fixed, the arm (1) having a holder portion for fixing a drape (9) in such a way that the microscope (3) and the holder portion are substantially air-tightly enclosed, the arm (1) including a carrier and a cladding releasably fixed to the carrier;
    a cable duct (2) in the arm (1) between the carrier and the cladding, the cable duct (2) having a front portion (10) that extends forward from the holder portion for fixing the drape (9) and which is in communicating relationship with an intermediate space between the drape (9) and the microscope (3) or the holder portion, the cable duct (2) further having a rear portion (12) rearward of the holder portion;
    a pumping-out device (15) which comprises a suction hose that is arranged at least partly in the interior of the cable duct (2) for pumping air out of the front portion (10) and the intermediate space between the drape (9) and the microscope (3) or the holder portion; and
    at least one resiliently elastic seal in sealing engagement with inner peripheral surface regions of the cable duct across an entire cross section of the cable duct, the seal including passages for cables and the suction hose (15) and being arranged in the cable duct (2) at a position substantially aligned with the holder portion for fixing the drape (9) between the front portion (10) and the rear portion (12) to seal the front portion (10) from the rear portion (12) in a pumping-out operation by the pumping-out device (15) to prevent a flow of air from the rear portion into the front portion, the seal being pressed by virtue of a resilient elastic spring force thereof against an inside wall of the cladding when the cladding is fitted so that a lower output of the pumping out device (15) is required to offset a make-up flow of air into the intermediate space.

9. The microscope support stand of claim 8 characterised in that the at least one seal includes at least two seals (17, 19) each of which is in sealing engagement with inner peripheral surface regions of the cable duct across two entire cross sections of the cable duct, each of the seals (17, 19) having passages for the cables and the suction hose (15), the seals being arranged at an axial spacing from each other.

10. The microscope support stand of claim 8 wherein the elastic seal is an elastic foam seal.

11. The microscope support stand of claim 8 wherein the elastic seal consists of a unitary piece of elastic foam.

12. The microscope support stand of claim 8 wherein the elastic seal has opposite front and rear faces, the front face of the elastic seal facing into the front portion of the cable duct and the rear face of the elastic seal facing into the rear portion of the cable duct.

13. The microscope support stand of claim 8, wherein the arm further includes at least one marking at a location substantially aligned with the seals for identifying a position of the holder portion for fixing the drape (9).

* * * * *